US008900639B2

(12) United States Patent
Cheung

(10) Patent No.: US 8,900,639 B2
(45) Date of Patent: Dec. 2, 2014

(54) PROCESS FOR OBTAINING A RABBIT SKIN COMPRISING BIOLOGICAL ACTIVE SUBSTANCES

(71) Applicant: Vanworld Pharmaceutical (Rugao) Company Limited

(72) Inventor: Wing Sum Cheung, Rugao (CN)

(73) Assignee: Vanworld Pharmaceutical (Rugao) Company Limited, Rugao (CN)

(*) Notice: Subject to any disclaimer, the term of this patent is extended or adjusted under 35 U.S.C. 154(b) by 129 days.

(21) Appl. No.: 13/777,637

(22) Filed: Feb. 26, 2013

(65) Prior Publication Data

US 2013/0183386 A1 Jul. 18, 2013

Related U.S. Application Data

(63) Continuation of application No. 12/880,856, filed on Sep. 13, 2010, now abandoned, which is a continuation of application No. 10/532,687, filed as application No. PCT/CN03/00923 on Oct. 30, 2003, now abandoned.

(30) Foreign Application Priority Data

Oct. 31, 2002 (CN) ................................. 02 1 45975

(51) Int. Cl.

*A61K 35/36* (2006.01)
*A23J 1/10* (2006.01)
*A61K 35/12* (2006.01)
*A61K 39/285* (2006.01)
*A61K 39/00* (2006.01)

(52) U.S. Cl.

CPC . *A61K 35/36* (2013.01); *A23J 1/10* (2013.01); *A61K 39/285* (2013.01); *A61K 35/12* (2013.01); *A61K 2039/54* (2013.01)

USPC ......... 424/572; 424/93.1; 424/94.1; 435/325; 435/1.1; 530/412

(58) Field of Classification Search

CPC .............. A61K 2300/00; A61K 35/16; A61K 38/1709; A61K 38/00; A61K 38/1725; A61K 39/285; A61K 31/00; A61K 35/12; A61K 35/36; A61K 39/00; A61K 39/3955; A61K 9/0019; C07K 16/18; C07K 14/005

See application file for complete search history.

(56) References Cited

U.S. PATENT DOCUMENTS

| | | | |
|---|---|---|---|
| 3,455,784 | A | 7/1969 | Album et al. |
| 3,949,073 | A | 4/1976 | Daniels et al. |
| 4,490,359 | A | 12/1984 | Kimura |
| 4,798,171 | A | 1/1989 | Peters et al. |
| 5,057,324 | A | 10/1991 | Shibayama et al. |
| 5,225,331 | A | 7/1993 | Jennings et al. |
| 5,960,635 | A | 10/1999 | Dakhil |
| 6,019,988 | A | 2/2000 | Parab et al. |

FOREIGN PATENT DOCUMENTS

| | | |
|---|---|---|
| CN | 1055249 C | 8/2000 |
| FR | 2564320 | 11/1985 |
| WO | WO03053463 | 7/2003 |
| WO | 2004060381 | 7/2004 |

OTHER PUBLICATIONS

Friedman-Kien AE, Fondak AA, Klein RJ. Phosphonoacetic acid treatment of shope fibroma and vaccinia virus skin infections in rabbits. J Invest Dermatol. Feb. 1976;66(02):99-102.*

Encyclopedia Britannica Company, Dictionary of Arts, Sciences, Literature and General Information, Eleventh Edition, vol. Ii (the Encyclopedia Britannica Company, New York, 1910), p. 860. 1 1.

Kister, Henry Z., Distillation Design (McGraw-Hill) p. 4, Copyright 1992 by McGraw-Hill.

* cited by examiner

*Primary Examiner* — Benjamin P Blumel
*Assistant Examiner* — Rachel Gill
(74) *Attorney, Agent, or Firm* — Greer, Burns & Crain, Ltd.

(57) ABSTRACT

The present invention relates to a process for obtaining a rabbit skin containing biologically active substances. The rabbit skin extract is obtained by the process including vaccinating a rabbit subcutaneously with vaccinia virus, feeding the rabbit, killing the rabbit when the skin is inflamed, skinning the rabbit within 15 minutes of death, preserving the rabbit skin at −18 degrees Celsius, extracting a portion of the rabbit skin with a phenol solution at 4° C., processing the rabbit skin extract with an acid and an alkali, eluting the rabbit skin extract and fractioning under a nitrogen atmosphere the eluted portion of the rabbit skin extract. The rabbit skin of the present invention can be used for preparing drugs and health foods.

4 Claims, No Drawings

PROCESS FOR OBTAINING A RABBIT SKIN COMPRISING BIOLOGICAL ACTIVE SUBSTANCES

This application is a continuation application of and claims the benefit of U.S. patent application Ser. No. 12/880,856, which claims priority from U.S. patent application Ser. No. 10/532,687 filed on Apr. 26, 2005, which claims priority from International Application No. PCT/CN2003/000923, filed on Oct. 30, 2003, each application being incorporated herein in their entireties.

DESCRIPTION

A rabbit skin containing biologically active substances and its use.

FIELD OF THE INVENTION

The present invention relates to a rabbit skin containing biologically active substances and its use.

BACKGROUND OF THE INVENTION

It was reported that the extracts from inflammatory rabbit skin tissues vaccinated with vaccinia virus can be used for the treatment of allergic disease and have analgesic effects. There has not been any method to prepare rabbit skin that contains strongly active and high yield biologically active substances.

DETAILED DESCRIPTION OF THE INVENTION

Aims

The objective of the present invention is to provide a rabbit skin which is rich in biologically highly active substances that can be used for preparing drugs and health foods.

Project

As a result of many years of hard work, the inventors of the present invention have reached this aim.

The rabbit skin of the present invention is obtained by the process including vaccinating rabbit (*Oryctolagus cuniculus*) skin tissues with vaccinia virus, feeding rabbit vaccinated with vaccinia virus, killing the rabbit when its skin tissues are sufficiently inflamed, and peeling or skinning the rabbit.

Vaccinia virus has been used widely since the 20th century. All kinds of vaccinia virus can be used to prepare the rabbit skin of the present invention, such as Lister strain, Ikeda strain, Dairen strain, EM-63 strain, Temple of Heaven strain, LMC strain, Tashkent strain, Williamsport strain, and New York City Board of Health strain. The preferred strains are Lister strain, Ikeda strain, Dairen strain, EM-63 strain, and the most preferred strain is Lister strain. All these vaccinia virus strains can be commercially purchased. The vaccinia virus strains used in the present invention can be purchased strain or strain obtained from subculture with a rabbit.

The preferred vaccination method is subcutaneous vaccination, the said vaccinating rabbit skin tissues with vaccinia virus is effected by injecting subcutaneously 0.1~0.4 ml solution containing $10^6$~$10^9$ viruses/ml each site, 100 to 250 sites per rabbit weighing 1.5~3 Kg.

The rabbit used in preparing the rabbit skin of present invention can be all kinds of rabbits, such as Japanese white rabbit, New Zealand white rabbit, Chinese rabbit, Chinchilla rabbit, Silver Fox rabbit, Viennese rabbit, Long hair rabbit, Himalayan albio rabbit, Pex, Belgian Hare rabbit, Lop, California rabbit, Chekered Giant, Denmark white rabbit, West Germany long hair rabbit, the preferred rabbits are Japanese white rabbit, New Zealand white Rabbit, Chinese rabbit, Chinchilla rabbit, the most preferred rabbit is Japanese white rabbit.

The said killing the rabbit when its skin tissues are sufficiently inflamed is effected when the rabbit skin inflammatory tissue shows visible blains accompanying with changing colour from redness to mauveness and becomes thick, and its subcuticle and hip become swollen. The preferred method to kill rabbit is cervical vertebrae dislocation.

Effect

The rabbit skin of the present invention possesses 0.5 iu/g SART activity or more, and which also possesses kallikrein production inhibition activity.

By extracting with organic solvent, processing with acid, processing with alkali, absorbing, eluting and concentrating, biologically active preparations being rich in amino acids and nucleic acids can be prepared from the rabbit skin. The said amino acids include glutamic acid, glycine, alanine, valine, isoleucine, leucine, tyrosine, phenylalanine, lysine, histidine, aspartic acid, threonine and serine. The said nucleic acids include urocanic acid, uracil, hypoxanthine, xanthine and thymine.

A drug can be prepared by combining the biologically active preparations of the present invention with pharmaceutical acceptable adjuvants. This drug can be one of various forms of preparations used clinically, including injections and tablets, the preferred form is injections. For injections, the adjuvants can be for example injectable distilled water, normal saline, injectable vegetable oil, glucose injection, propylene glycol, polyethylene glycol, or it may be all kinds of stabilizers and emulsifiers. For tablets, capsules and granules, the adjuvants can be excipients such as starch, lactose, mannitol; binders such as crystalline cellulose, arabic gum, corn starch, glutin, polyethylene, polyvinyl alcohol, polyvinylpyrrolidone; disintegrants such as carboxyl methyl cellulose, poly-ethylene glycol, potato starch; lubricants such as talcum powder, magnesium stearic acid; moistening agents such as glycerol. For ointments, the adjuvants can be fat oil, paraffin, wool fat, Vaseline, glycol, glycerol.

Pharmacological and clinical experiments showed that the drugs prepared from the rabbit skin of the present invention have analgesic effect against all kinds of symptomatic neuralgia, lambago, cholecystagia, angina, arterial embolism pains, acute pains from wound, burn and scald, pains in surgery or post-surgery, peptic ulcer pain, dysmenorrhea, labor pains posterior to childbirth, headache, pains induced by various tumor and so on.

The study showed that the drugs prepared from the rabbit skin of the present invention can effectively promote activation of macrophage, significantly inhibit 48-hour homologous PCA reaction induced by antibody of IgE in the model of type I allergic reaction in mice, inhibit the activity of anti-complement in type II allergic reaction. The effects have linear correlation with the doses. So the drugs have effects on inhibiting inflammatory reaction correlated with immunity and improving immunity function.

Moreover, the drugs prepared from the rabbit skin of the present invention have anti-allergic, anti-ulcer and sedative effects and so on.

After a continuous 28-day intraperitoneally administration of the drugs prepared from the rabbit skin of the present invention in rats, no rats died and no changes induced by the drugs existed in examinations of urine, eye, blood biochemistry, pathology and anatomy. Therefore, the analgesic drugs of the present invention have little toxic effects.

Health food can be prepared by combining the biologically active preparations of the present invention with edible additives and nutritious substances, the said edible additives and nutritious substances include all kinds of vitamins and flavoring agents and so on. These kinds of health food have effects on improving immunity, alleviating pains, anti-allergy and anti-stress and so on.

The method of determination of SART (Specific Alteration of Rhythm in Environmental Temperature) activity is well known in the art (Folia pharmacol. japon. 71:211~220, 1975).

The kallikrein production inhibition activity referred in this description is determined as follows.

The rabbit skin was cut in pieces of 1 $cm^2$, 4 times (w/w) of 3% phenol aqueous solution was added, and then the mixture was placed at 4° C. for 72 h, and centrifuged after liquid changed into an emulsion. The supernatant was filtrated to collect brown solution A. The brown solution A was boiled for 40 min in a water bath after pH was adjusted to 5.0 by 1M HCl, cooled to 28° C. promptly, centrifuged and filtrated to collect solution B. The solution B was boiled for 40 min in a water bath after pH of filtrate was adjusted to 9.2 by 1M NaOH, cooled to 28° C. promptly, and filtrated to collect solution C. The pH of the solution C was adjusted to 4.5 by 1M HCl, activated charcoal was added at 30° C., stirred continuously for 4 h. After stirring was terminated, the solution was left for 30 min. The supernatant was then removed and filtrated under a nitrogen atmosphere. Then, the activated charcoal was dipped in injectable water and washed, filtrated and the filtrate was discarded to collect the activated charcoal, while reserving the activated charcoal. The activated charcoal was then put into injectable water, pH was adjusted to 11.0 by 1M NaOH, the solution was stirred continuously for 4 h, filtrated with a 0.45-μm Millipore filter under nitrogen atmosphere, and the activated charcoal was washed by injectable water to collect solution D. After pH of the solution D was adjusted to 6.0 by 1M HCl, the vessel was sealed, heated up and maintained at 121° C. for 20 min, and then cooled down to under 40° C. to collect solution E. The solution E was placed into a decompression distillator, the air was replaced with nitrogen in the decompression distillator, the solution was distilled at 60° C. under decompression, and filtrated to collect a solution containing biologically active substances, whose SART activity was determined. The SART activity of the solution was adjusted to 1.2 iu/ml by evaporating, concentrating and diluting with distilled water. Next, 10 ml of this solution was desalted at 10 μs/cm of final conductance, and dried under decompression condition, into which 1.5 ml of 0.25 M NaCl solution was added to obtain a test solution. Next, 0.2 ml of 0.25M NaCl solution was regarded as the control solution and treated with a parallel process with the 0.2 ml test solution. Then, 0.5 ml of human plasma was added respectively to both solutions, placed at the freezing point for 5 min, 0.25 ml of suspension of argilla was added, placed at the freezing point for 20 min, and filtrated. 0.1 ml of filtrate was mixed with 0.2 ml of 0.1 M Tris-HCl buffer and 0.1 ml of basic solution. The reaction was effected for 20 min at 30° C., and was stopped by adding 0.8 ml of 1% citric acid. The absorbance A of the test solution was determined in a control solution with 405 nm as the absorbance and was initialized as 0.4. If A was less than 0.4, the rabbit skin from which the test solution was prepared was regarded as possessing the kallikrein production inhibition activity.

EXAMPLES

The present invention will be illustrated with following non-limited examples.

Example 1

Preparation of Rabbit Skin

The dry variola vaccine of vaccinia virus Lister strain was dissolved by PBS(−) (NaCl 80 g, KCl 2 g, NaH2PO4 11.5 g, KH2PO4.2H2O 2 g, adding injectable H2O to 10 L) and well shaken. 0.4 ml of this solution was injected in the central inner lamina of testicle of a Japanese white rabbit. Dislocating its cervical vertebra on the fourth day, the scrotum was cut and connective tissue in the testicle was removed. The testicle was placed in a vessel full of ice, preserved at −80° C. in a refrigerator. The testicle was taken from the refrigerator, softened for 1 h, ground at 4° C., mixed in 1:1 with EAGLES' cultural medium (Eagle's powder 9.4 g, 10% NaHCO3 12.5~22.0 ml, glutamine 10 ml, injectable H2O 1 L), packed, frozen at −80° C. in refrigerator for 1 h, thawed at 37° C. in water bath, centrifuged with 3500 rpm at 4° C. for 20 min, packed by 10 ml. The subculture antigen was preserved at −80° C. in refrigerator.

The virus solution of the subculture antigen was taken from the −80° C. refrigerator, and was thawed at 30° C. in an incubator. Then, 5 ml of the virus solution was added to 500 ml of PBS(−) by a 10-ml syringe, and was well shaken and diluted to an injection of 109 virus/ml. A Japanese white rabbit, weighing 3 kg, with its back shaved, was sterilized with 75% ethanol, injected subcutaneously with the virus injection of 0.4 ml per site in 200 sites with no leaking, no injecting without the virus injection and no puncturing throughout the skin. The injected rabbit was fed for 4 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and was preserved at −18° C. in a refrigerator prior to use. The rabbit skin weighed 349 g, its SART activity was 0.85 iu/g, and its absorbance was 0.07. The results indicated that it possessed the kallikrein production inhibition activity.

Example 2

Preparation of Rabbit Skin

The vaccinia virus Ikeda strain and New Zealand white rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^9$ virus/ml. A New Zealand white rabbit, weighing 2.75 kg, with its back shaved, was sterilized with 75% ethanol, injected subcutaneously with the virus injection of 0.3 ml per site in 250 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 302 g, its SART activity was 0.60 iu/g, and its absorbance was 0.1. The results indicated that it possessed the kallikrein production inhibition activity.

Example 3

Preparation of Rabbit Skin

The vaccinia virus Dairen strain and Chinese rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^6$ virus/ml. A Chinese rabbit weighing 1.5 kg, with its back shaved, was sterilized with 75% ethanol, injected subcutaneously with the virus injection of 0.1 ml per site in 250 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by cervical vertebra dislocation and it was peeled after 15 min. The skin of the rabbit was packed in a plastic bag, and preserved at −18° C. in a refrigerator prior to use. The skin of the rabbit weighed 176 g, its SART activity was 0.50 iu/g, and its absorbance was 0.15. The results indicated that it possessed the kallikrein production inhibition activity.

Example 4

Preparation of Rabbit Skin

The vaccinia virus EM-63 strain and Chinchilla rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^7$ virus/ml. A Chinchilla rabbit, weighing 2 kg with its back shaved, was sterilized with 75% ethanol, injected subcutaneously with the virus injection of 0.2 ml per site in 100 sites with no leaking, no injecting without the virus injection and no puncturing throughout skin. The injected rabbit was fed for 3 days. When inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 230 g, its SART activity was 0.55 iu/g, and its absorbance was 0.12. The results indicated that it possessed the kallikrein production inhibition activity.

Example 5

Preparation of Rabbit Skin

The vaccinia virus Lister strain and New Zealand white rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^9$ virus/ml. A New Zealand white rabbit, weighing 2.75 kg, with its back shaved, was sterilized with 75% ethanol, injected subcutaneously with the virus injection of 0.3 ml per site in 200 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of rabbit was packed in a plastic bag, and it was preserved at −18° C. in a refrigerator prior to use. The skin of the rabbit weighed 310 g, its SART activity was 0.79 iu/g, and its absorbance was 0.09. The results indicated that it possessed the kallikrein production inhibition activity.

Example 6

Preparation of Rabbit Skin

The vaccinia virus Lister strain and Chinese rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^6$ virus/ml. A Chinese rabbit, weighing 1.5 kg, with its back shaved, was sterilized with 75% ethanol, injected subcutaneously with the virus injection of 0.1 ml per site in 250 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 185 g, its SART activity was 0.71 iu/g, and its absorbance was 0.11. The results indicated that it possessed the kallikrein production inhibition activity.

Example 7

Preparation of Rabbit Skin

The vaccinia virus Lister strain and Chinchilla rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^7$ virus/ml. A Chinchilla rabbit, weighing 2 kg, with its back shaved, was sterilized with 75% ethanol, injected subcutaneously with the virus injection of 0.2 ml per site in 100 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 235 g, its SART activity was 0.74 iu/g, and its absorbance was 0.13. The results indicated that it possessed the kallikrein to production inhibition activity.

Example 8

Preparation of Rabbit Skin

The vaccinia virus Ikeda strain and Japanese white rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml PBS (−) by a 10-ml syringe, and was well shaken and diluted to an injection of $10^9$ virus/ml. A Japanese white rabbit, weighing 3 kg, with its back shaved, was sterilized with 75% ethanol, injected subcutaneously with the virus injection of 0.3 ml per site in 200 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 335 g, its SART activity was 0.70 iu/g, and its absorbance was 0.12. The results indicated that it possessed the kallikrein production inhibition activity.

Example 9

Preparation of Rabbit Skin

The vaccinia virus Dairen strain and Japanese white rabbit were used to prepare for the subculture antigen according to example 1.

The virus solution of the subculture antigen was taken from the −80° C. refrigerator, and was thawed at 30° C. in an incubator. Next, 5 ml of the virus solution was added to 500 ml of PBS (−) by a 10-ml syringe, and was well shaken and diluted to an injection of $10^6$ virus/ml. A Japanese white rabbit, weighing 3 kg, with its back shaved, was sterilized with 75% ethanol, injected subcutaneously with the virus injection of 0.1 ml per site in 200 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 336 g, its SART activity was 0.61 iu/g, and its absorbance was 0.14. The results indicated that it possessed the kallikrein production inhibition activity.

Example 10

Preparation of Rabbit Skin

The vaccinia virus EM-63 strain and Japanese white rabbit were used to prepare the subculture antigen according to example 1.

The virus solution of the subculture antigen was taken from the −80° C. refrigerator, and was thawed at 30° C. in an incubator. Next, 5 ml of the virus solution was added to 500 ml of PBS(−) by a 10-ml syringe, and was well shaken and diluted to an injection of $10^7$ virus/ml. A Japanese white rabbit, weighing 3 kg, while its back was shaved, was sterilized with 75% ethanol, injected subcutaneously with the virus injection of 0.2 ml per site in 200 sites with no leaking, no injecting without the virus injection and no puncturing throughout skin. The injected rabbit was fed for 3 days. When the inflammatory tissue showed that the skin surface had visible blains accompanied by changing colour from redness to mauveness, the skin became thick, and the subcuticle and the hip became swollen, the rabbit was killed by dislocating the cervical vertebra and it was peeled after 15 min. The skin of the rabbit was packed in a plastic bag, and preserved at −18° C. in a refrigerator prior to use. The skin of the rabbit weighed 335 g, its SART activity was 0.66 iu/g, and its absorbance was 0.12. The results indicated that it possessed the kallikrein production inhibition activity.

Example 11

Extraction of Bioactive Substances.

200 g each of the rabbit skins prepared according to example 1~10 were cut into pieces of 1 $cm^2$, added into 4 times (w/w) of 3% phenol solution, placed at 4° C. for 72 h, centrifuged after liquid changed into emulsion. The centrifuged liquid was filtrated to collect brown solution A. After solution A's pH was adjusted to 5.0 by 1M HCl, boiled solution A in a water bath for 40 min and cooled down to 28° C. immediately, centrifuged, and filtrated to collect solution B. After pH of filtrate was adjusted to 9.2 by 1M NaOH, the solution B was boiling for 40 min in a water bath, cooled down to 28° C. immediately, and filtrated to collect solution C. After pH of filtrate was adjusted to 4.5 by 1M HCl, 50 g of activated charcoal was added to the solution C at 30° C., stirred continuously for 4 h, stopped stirring, left it for 30 min, removed the supernatant, filtrated under nitrogen atmosphere. The activated charcoal was dipped in injectable water and washed, filtrated and removed filtrate to collect and reserve the activated charcoal. The activated charcoal was then added into 400 ml injectable water in which pH was adjusted to 11.0 by 1M NaOH, stirred continuously for 4 h, filtrated with a 0.45-μm Millipore filter under nitrogen atmosphere, washed by 40 ml of injectable water to collect solution D. After pH of the solution D was adjusted to 6.0 by 1M HCl, the vessel was sealed, heated up and kept the temperature at 121° C. for 20 min and cooled down to under 40° C. to collect solution E. The solution E in decompression distillator under nitrogen was decompressed and evaporated at 60° C. till the volume was 5 ml and filtrated to collect preparation of 5 ml of solution containing bioactive substances. The content of amino acids and nucleic acids below were determined (μg/ml):

| Sample | Exam. 1 | Exam. 2 | Exam. 3 | Exam. 4 | Exam. 5 | Exam. 6 | Exam. 7 | Exam. 8 | Exam. 9 | Exam. 10 |
|---|---|---|---|---|---|---|---|---|---|---|
| Glutamic acid | 1.64 | 0.85 | 0.70 | 0.80 | 1.54 | 1.20 | 1.40 | 1.12 | 0.98 | 1.03 |
| Glycine | 0.92 | 0.51 | 0.33 | 0.49 | 0.86 | 0.73 | 0.80 | 0.70 | 0.55 | 0.61 |
| Alanine | 0.96 | 0.64 | 0.59 | 0.60 | 0.92 | 0.77 | 0.83 | 0.76 | 0.66 | 0.70 |
| Valine | 0.66 | 0.34 | 0.23 | 0.29 | 0.62 | 0.57 | 0.61 | 0.51 | 0.39 | 0.45 |
| Isoleucine | 0.42 | 0.17 | 0.10 | 0.14 | 0.40 | 0.32 | 0.38 | 0.30 | 0.26 | 0.28 |
| Leucine | 0.67 | 0.22 | 0.11 | 0.16 | 0.66 | 0.53 | 0.60 | 0.46 | 0.35 | 0.41 |
| Tyrosine | 0.83 | 0.30 | 0.25 | 0.20 | 0.77 | 0.61 | 0.69 | 0.52 | 0.36 | 0.44 |
| Phenylalanine | 0.55 | 0.26 | 0.24 | 0.25 | 0.53 | 0.42 | 0.48 | 0.34 | 0.30 | 0.33 |
| Lysine | 0.47 | 0.11 | 0.09 | 0.10 | 0.45 | 0.39 | 0.34 | 0.34 | 0.19 | 0.26 |
| Histidine | 0.64 | 0.24 | 0.18 | 0.21 | 0.57 | 0.43 | 0.53 | 0.41 | 0.31 | 0.35 |

-continued

| Sample | Exam. 1 | Exam. 2 | Exam. 3 | Exam. 4 | Exam. 5 | Exam. 6 | Exam. 7 | Exam. 8 | Exam. 9 | Exam. 10 |
|---|---|---|---|---|---|---|---|---|---|---|
| Aspartic acid | 0.68 | 0.44 | 0.39 | 0.40 | 0.61 | 0.57 | 0.58 | 0.49 | 0.45 | 0.46 |
| Threonine | 0.51 | 0.24 | 0.11 | 0.16 | 0.50 | 0.42 | 0.46 | 0.38 | 0.30 | 0.34 |
| Serine | 1.01 | 0.69 | 0.66 | 0.67 | 0.98 | 0.79 | 0.88 | 0.75 | 0.70 | 0.71 |
| Urocanic acid | 25.00 | 13.24 | 12.52 | 13.00 | 24.75 | 22.39 | 24.00 | 20.01 | 16.55 | 17.64 |
| Uracil | 16.12 | 6.66 | 5.51 | 6.16 | 14.31 | 10.46 | 13.19 | 10.00 | 7.12 | 8.54 |
| Hypoxanthine | 1.71 | 0.85 | 0.80 | 0.81 | 1.65 | 1.11 | 1.34 | 1.01 | 0.89 | 0.99 |
| Xanthine | 12.44 | 6.13 | 5.21 | 5.79 | 12.00 | 9.98 | 11.67 | 9.62 | 6.39 | 8.13 |
| Thymine | 3.38 | 1.99 | 1.15 | 1.54 | 3.30 | 2.77 | 3.19 | 2.49 | 2.04 | 2.44 |

Example 12

Preparation of Drug

The analgesic injection was prepared by the formula below using the regular method.

| | |
|---|---|
| Preparation from rabbit skin according to example 2 | 5 ml |
| NaCl | 2.6 g |
| Injectable distilled water | 300 ml |

Example 13

Preparation of Tablet

The analgesic tablet was prepared by the formula below using the regular method.

| | |
|---|---|
| Preparation from rabbit skin according to example 1 | 50 ml |
| Lactose | 125 mg |
| Crystalline cellulose | 20 g |
| Magnesium stearic acid | 5 mg |

Example 14

Preparation of Health Food

The health food was prepared by the formula below using the regular method.

| | |
|---|---|
| Preparation from rabbit skin according to example 1 | 50 ml |
| Sucrose | 125 mg |
| Citric acid | 20 mg |
| Vitamin C | 5 mg |
| Water | 1000 ml |

The invention claimed is:

1. A process for obtaining a rabbit skin extract, said process comprising:

i) inoculating a rabbit subcutaneously with a vaccinia virus, wherein said subcutaneous injection is 0.1-0.4 ml of a vaccinia virus solution containing $10^6$-$10^9$ viral particles per one milliliter per each injection site, wherein the total number of injections is from 100 to 250 per rabbit, wherein the rabbit weighs 1.5-3 kg;

ii) feeding and monitoring the rabbit for at least 72 hours to monitor development of skin inflammation;

iii) sacrificing the rabbit between 72 and 96 hours after inoculation;

iv) harvesting the inflamed rabbit skin within 15 minutes of step iii) and preserving the inflamed rabbit skin at 18 degree C;

v) obtaining a rabbit skin extract by treating the inflamed rabbit skin obtained in step iv) with a 3% phenol solution at 4 degree C. for at least 72 hours, wherein the ratio between said rabbit skin and said phenol solution is at least 1:4 by weight;

vi) processing said rabbit skin extract from step v) to obtain a rabbit skin extract with a pH of 4.5;

vii) incubating said processed rabbit skin extract from step vi) with activated charcoal;

viii) eluting said processed rabbit skin extract from the activated charcoal from step vii) under a basic pH, thereby obtaining the rabbit skin extract.

2. The process of claim 1, wherein the vaccinia virus is selected from the group consisting of Lister strain, Ikeda strain, Dairen strain and EM-63 strain.

3. The process of claim 1, wherein the rabbit is selected from the group consisting of a Japanese white rabbit, a New Zealand white rabbit, a Chinese rabbit, and a Chinchilla rabbit.

4. The process of claim 1, wherein the rabbit exhibits the following symptoms: the inflamed skin is erythematous and shows visible blains or sores, and the subcuticles and hips of the rabbit become swollen.

* * * * *

UNITED STATES PATENT AND TRADEMARK OFFICE

CERTIFICATE OF CORRECTION

PATENT NO. : 8,900,639 B2
APPLICATION NO. : 13/777637
DATED : December 2, 2014
INVENTOR(S) : Wing Sum Cheung It is certified that error appears in the above-identified patent and that said Letters Patent is hereby corrected as shown below:

In the Claims

In line 14 of claim 1, delete "18" and please insert -- "-18" --.

Claim 1 should read as follows:

"A process for obtaining a rabbit skin extract, said process comprising:

i) inoculating a rabbit subcutaneously with a vaccinia virus, wherein said subcutaneous injection is 0.1-0.4 ml of a vaccinia virus solution containing $10^6$-$10^9$ viral particles per one milliliter per each injection site, wherein the total number of injections is from 100 to 250 per rabbit, wherein the rabbit weighs 1.5-3 kg;

ii) feeding and monitoring the rabbit for at least 72 hours to monitor development of skin inflammation;

iii) sacrificing the rabbit between 72 and 96 hours after inoculation;

iv) harvesting the inflamed rabbit skin within 15 minutes of step iii) and preserving the inflamed rabbit skin at -18 degree C.;

v) obtaining a rabbit skin extract by treating the inflamed rabbit skin obtained in step iv) with a 3% phenol solution at 4 degree C. for at least 72 hours, wherein the ratio between said rabbit skin and said phenol solution is at least 1:4 by weight;

vi) processing said rabbit skin extract from step v) to obtain a rabbit skin extract with a pH of 4.5;

vii) incubating said processed rabbit skin extract from step vi) with activated charcoal;

viii) eluting said processed rabbit skin extract from the activated charcoal from step vii) under a basic pH, thereby obtaining the rabbit skin extract."

Signed and Sealed this
Tenth Day of May, 2016

Michelle K. Lee

Michelle K. Lee
*Director of the United States Patent and Trademark Office*